(12) United States Patent
Hotta et al.

(10) Patent No.: US 10,241,385 B2
(45) Date of Patent: Mar. 26, 2019

(54) DISPLAY DEVICE AND MEDICAL DIAGNOSTIC IMAGING DEVICE

(71) Applicant: Canon Medical Systems Corporation, Otawara-shi, Tochigi-Ken (JP)

(72) Inventors: Aira Hotta, Kanagawa (JP); Takashi Sasaki, Kanagawa (JP); Kazuo Horiuchi, Kanagawa (JP); Sayaka Takai, Kanagawa (JP); Tomoya Tsuruyama, Kanagawa (JP)

(73) Assignee: Canon Medical Systems Corporation, Otawara-shi, Tochigi-Ken (JP)

( * ) Notice: Subject to any disclaimer, the term of this patent is extended or adjusted under 35 U.S.C. 154(b) by 76 days.

(21) Appl. No.: 15/098,469

(22) Filed: Apr. 14, 2016

(65) Prior Publication Data

US 2016/0313634 A1    Oct. 27, 2016

(30) Foreign Application Priority Data

Apr. 21, 2015 (JP) ................. 2015-087125

(51) Int. Cl.
| | |
|---|---|
| *G03B 21/28* | (2006.01) |
| *G01R 33/28* | (2006.01) |
| *G02B 5/10* | (2006.01) |
| *G02B 5/09* | (2006.01) |
| *G02B 3/08* | (2006.01) |
| *G03B 21/14* | (2006.01) |
| *A61B 5/055* | (2006.01) |
| *A61B 5/00* | (2006.01) |

(52) U.S. Cl.
CPC ............ *G03B 21/28* (2013.01); *A61B 5/0555* (2013.01); *G01R 33/283* (2013.01); *G02B 3/08* (2013.01); *G02B 5/09* (2013.01); *G02B 5/10* (2013.01); *G03B 21/142* (2013.01); *A61B 5/7445* (2013.01)

(58) Field of Classification Search
CPC ....... A61B 5/0555; A61B 5/7445; A61B 5/00; G01R 33/283; G01R 33/28; G02B 3/08; G02B 5/09; G02B 5/08; G03B 21/142; G03B 21/28; H04N 7/18
USPC .......................................... 353/98
See application file for complete search history.

(56) References Cited

U.S. PATENT DOCUMENTS 3,085,470 A * 4/1963 Berger ................... G03B 21/00
                                                           352/167
5,047,640 A * 9/1991 Brunnschweiler ..........................
                                                           G01N 21/8915
                                                           250/341.8

(Continued)

FOREIGN PATENT DOCUMENTS

| JP | 2842998 | 10/1998 |
|---|---|---|
| JP | 2009-128565 | 6/2009 |

(Continued)

*Primary Examiner* — Steven H Whitesell Gordon
*Assistant Examiner* — Jerry Brooks
(74) *Attorney, Agent, or Firm* — Nixon & Vanderhye, P.C.

(57) ABSTRACT

According to an embodiment, a display device includes a reflecting member and a display. The reflecting member has a reflecting surface and has an optical property that reflected light of parallel light incident on the reflecting surface is focused a focal point. The reflecting member is fixed to a couch top on which a user lies down. The display has a display surface for displaying an image. The display is fixed to the couch top so that the display surface is positioned between the focal point and the reflecting surface to face the reflecting surface.

15 Claims, 9 Drawing Sheets

(56) References Cited

U.S. PATENT DOCUMENTS

| | | | |
|---|---|---|---|
| 5,877,732 A | 3/1999 | Ziarati | |
| 6,405,072 B1 * | 6/2002 | Cosman | A61N 5/1049 600/426 |
| 2006/0079763 A1 * | 4/2006 | Jeung | A61B 6/032 600/428 |
| 2006/0285089 A1 * | 12/2006 | Higashi | G03B 21/53 353/101 |
| 2007/0165779 A1 * | 7/2007 | Chen | A61N 5/1049 378/65 |
| 2010/0214635 A1 * | 8/2010 | Sasaki | G02B 27/0101 359/15 |
| 2011/0228403 A1 * | 9/2011 | Masuda | B60R 1/001 359/630 |
| 2013/0077175 A1 | 3/2013 | Hotta et al. | |
| 2013/0235168 A1 | 9/2013 | Gillies et al. | |
| 2015/0268547 A1 * | 9/2015 | Miesak | G03B 21/26 353/36 |
| 2015/0301339 A1 * | 10/2015 | Harris | G06F 1/1601 345/648 |
| 2016/0313635 A1 | 10/2016 | Sasaki et al. | |

FOREIGN PATENT DOCUMENTS

| | | |
|---|---|---|
| JP | 2012-123393 | 6/2012 |
| JP | 2013-073070 | 4/2013 |
| JP | 2013-546024 | 12/2013 |
| JP | 2016-202515 | 12/2016 |

\* cited by examiner

DISPLAY DEVICE AND MEDICAL DIAGNOSTIC IMAGING DEVICE

CROSS-REFERENCE TO RELATED APPLICATION

This application is based upon and claims the benefit of priority from Japanese Patent Application No. 2015-087125, filed on Apr. 21, 2015; the entire contents of which are incorporated herein by reference.

FIELD

Embodiments described herein relate generally to a display device and a medical diagnostic imaging device.

BACKGROUND

Medical diagnostic imaging devices are known that make use of X-rays or magnetism, such as computed tomography (CT) or magnetic resonance imaging (MRI). In such a diagnostic device, a user is asked to remain positioned inside a gantry for the purpose of taking images of that user. However, that may bring an oppressive feeling to the user.

In that regard, a technology is known by which images are projected on a wall surface of the room in which the medical diagnostic imaging device is installed, or a technology is known in which the user is asked to wear an eyepiece on the eyes and to watch a liquid crystal display via the eyepiece.

However, in the conventional technology, there are times when the images projected on the wall surface are not visible due to the material used to create the blocking space, or there are times when mounting the eyepiece brings an oppressive feeling. That is, in the conventional technology, it is difficult to sufficiently reduce the cooped-up feeling of the user.

DETAILED DESCRIPTION

According to an embodiment, a display device includes a reflecting member and a display. The reflecting member has a reflecting surface and has an optical property that reflected light of parallel light incident on the reflecting surface is focused a focal point. The reflecting member is fixed to a couch top on which a user lies down. The display has a display surface for displaying an image. The display is fixed to the couch top so that the display surface is positioned between the focal point and the reflecting surface to face the reflecting surface.

First Embodiment

Exemplary embodiments of a display device and a medical diagnostic imaging device are described below in detail with reference to the accompanying drawings.

In a first embodiment, the explanation is given for an example in which a display device is installed in a medical diagnostic imaging device.

Figure 1:
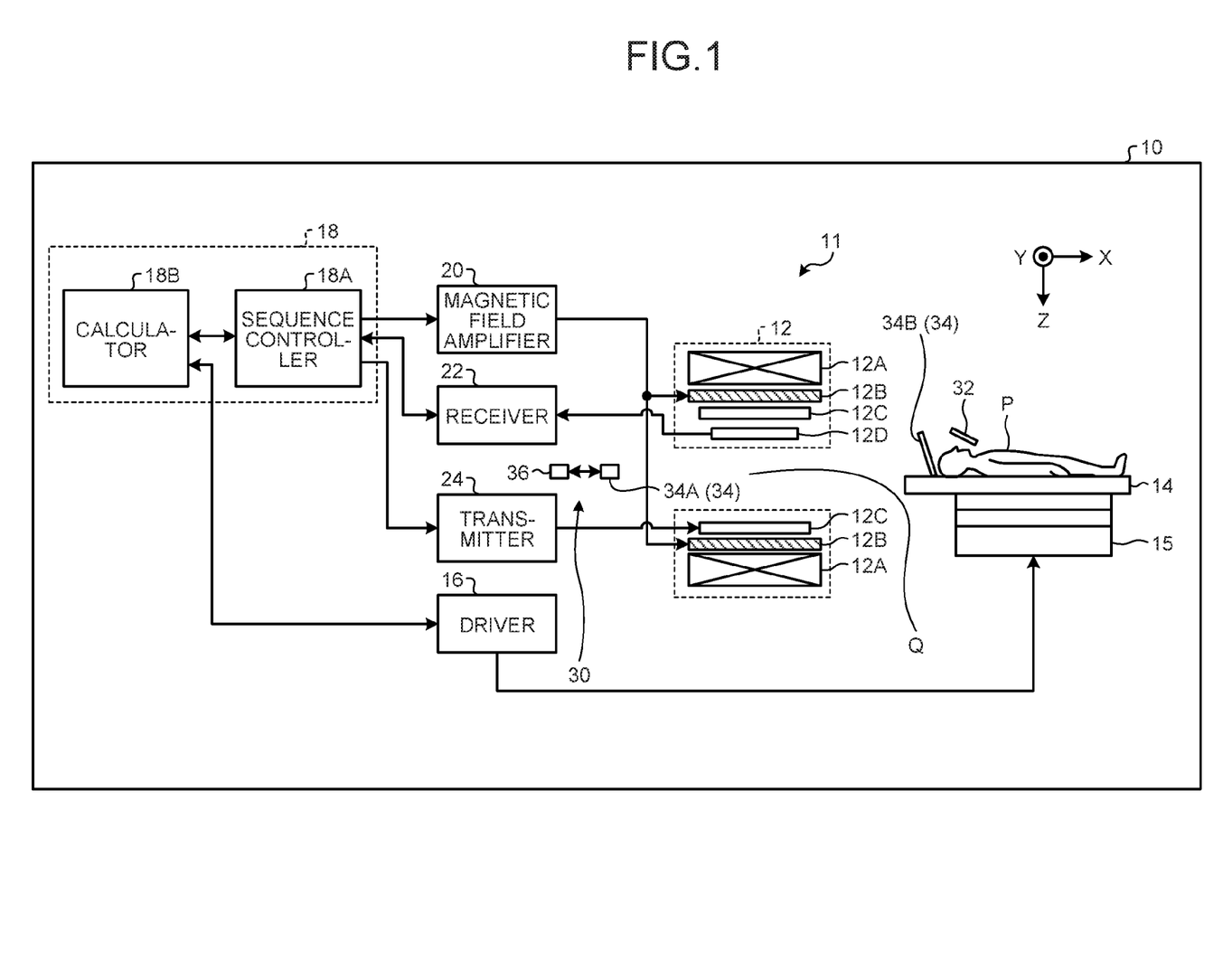
FIG. 1 is a schematic diagram illustrating an example of a medical diagnostic imaging device.

FIG. 1 is a schematic diagram illustrating an example of a medical diagnostic imaging device 10. Herein, the medical diagnostic imaging device 10 includes a medical diagnostic imaging unit 11 and a display device 30.

The medical diagnostic imaging unit 11 includes a tubular member 12, a couch top 14, a couch 15, a driver 16, a controller 18, a magnetic field amplifier 20, a receiver 22, and a transmitter 24.

The tubular member 12 is tubular in shape and includes a magnetic field generation source that forms a magnetic-field space. The tubular member 12 is sometimes also called a gantry. The couch top 14 is a plate-like member on which a user P to be diagnosed is asked to lie down. In the first embodiment, the explanation is given for a case in which the longitudinal direction (the X-axis direction) of the couch top 14 is coincident with the horizontal direction. Moreover, the explanation is given for a case in which the thickness direction (the Z-axis direction) of the couch top 14 is coincident with the vertical direction. Furthermore, the explanation is given for a case in which the width direction (the Y-axis direction) of the couch top 14 is orthogonal to the horizontal direction as well as the thickness direction. Meanwhile, as long as the X-axis direction, the Z-axis direction, and the Y-axis direction are orthogonal to each other, the X-axis direction need not be coincident with the horizontal direction and the Z-axis direction need not be coincident with the vertical direction.

The tubular member 12 includes a magnetostatic magnet 12A, a gradient coil 12B, a transmission coil 12C, and a receiving coil 12D.

The magnetostatic magnet 12A is formed in a hollow cylindrical shape, and generates a uniform magnetostatic field in the internal space. Examples of the magnetostatic magnet 12A include a permanent magnet and a superconducting magnet. The gradient coil 12B is disposed on the inside of the magnetostatic magnet 12A. Moreover, the gradient coil 12B is formed in a hollow cylindrical shape and generates a gradient magnetic field in the internal space. The transmission coil 12C is disposed on the inside of the gradient coil 12B. Moreover, the transmission coil 12C generates a high-frequency magnetic field.

For that reason, on the inside of the tubular member 12 (see a space Q), a magnetic-field space is created.

The receiving coil 12D is disposed on the inside of the gradient coil 12B. Moreover, the receiving coil 12D receives magnetic resonance signals (hereinafter, called MR signals). Herein, the receiving coil 12D receives MR signals irradiated from the user P due to the effect of the high-frequency magnetic field. Then, the receiving coil 12D outputs the received MR signals to the receiver 22. Meanwhile, the receiving coil 12D and the transmission coil 12C can be configured in an integrated manner as a transceiving coil.

The controller 18 includes a sequence controller 18A and a calculator 18B.

The calculator 18B performs comprehensive control of the medical diagnostic imaging unit 11 and generates MR images. The calculator 18B controls the sequence controller 18A and the driver 16.

The sequence controller 18A controls the magnetic field amplifier 20, the receiver 22, and the transmitter 24 based on sequence information sent from the calculator 18B. The sequence information represents information in which the procedure for imaging is defined. The sequence information contains the definition of the intensity of the electric current to be supplied to the magnetostatic magnet 12A or the timing of supplying the electric current to the magnetostatic magnet 12A; contains the definition of the intensity of radio frequency (RF) pulses that the transmitter 24 supplies to the transmission coil 12C or the timing of applying RF pulses; and contains the definition of the timing at which the receiver 22 detects MR signals.

More particularly, the sequence controller 18A sends control signals, which are based on the sequence information received from the calculator 18B, to the magnetic field amplifier 20, the receiver 22, and the transmitter 24.

According to the control signals sent by the sequence controller 18A, the magnetic field amplifier 20 supplies electrical power to the gradient coil 12B. Moreover, according to the control signals sent by the sequence controller 18A, the transmitter 24 sends RF pulses corresponding to the Larmor frequency to the transmission coil 12C. Furthermore, according to the control signals sent by the sequence controller 18A, the receiver 22 generates MR signal data based on the MR signals output from the receiving coil 12. More particularly, the receiver 22 performs digital conversion with respect to the MR signals output from the receiving coil 12D to generate MR signal data, and sends the MR signal data to the calculator 18B via the sequence controller 18A. The calculator 18B generates MR images from the MR signal data.

The driver 16 drives the couch 15, so that the couch top 14 moves in the X-axis direction thereof and the vertical direction. That is, the driver 16 moves the couch top 14 to the inside or the outside of the tubular member 12. As a result, the user P who is asked to lie down on the couch top 14 is inserted to the inside of the tubular member 12 or is carried to the outside from the inside of the tubular member 12. Meanwhile, the driver 16 can be alternatively disposed in the display device 30 (described later).

Figure 2:
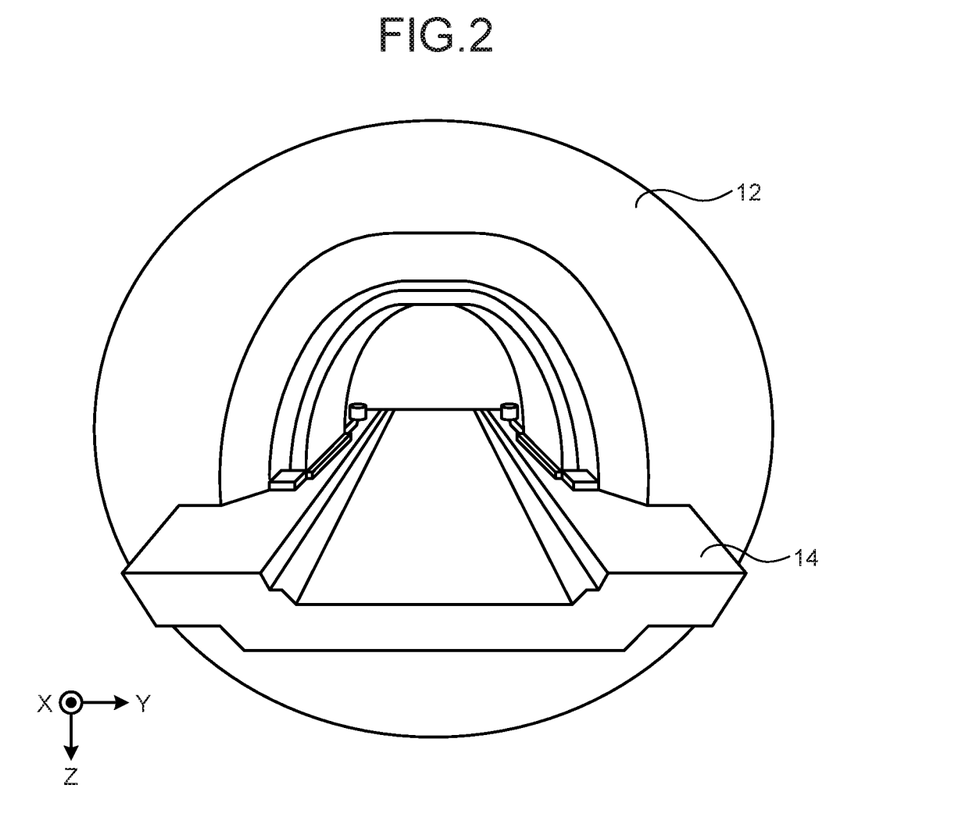
FIG. 2 is a schematic diagram illustrating the positional relationship between a tubular member and a couch top.

FIG. 2 is a schematic diagram illustrating the positional relationship between the tubular member 12 and the couch top 14. As illustrated in FIG. 2, the tubular member 12 is formed in a hollow cylindrical shape. The longitudinal direction of the couch top 14 and the longitudinal direction of tubular member 12 are coincident in the X-axis direction. The couch top 14 is disposed in a movable manner in the X-axis direction, and is inserted from one side of the X-axis direction to the inside of the tubular member 12 or is carried from the other side of the X-axis direction to the outside of the tubular member 12.

Figure 3:
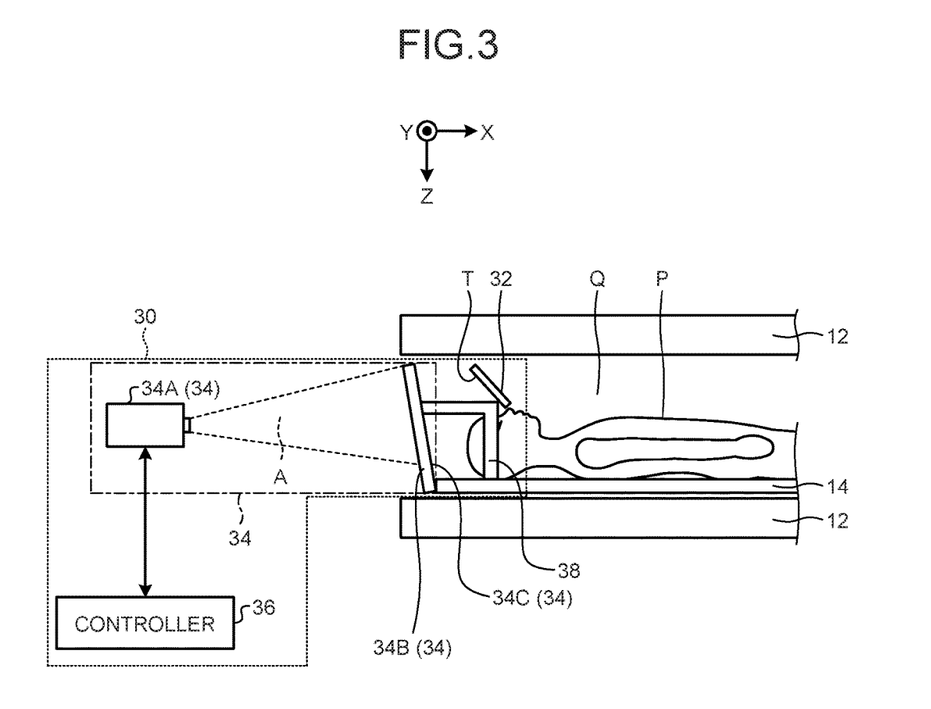
FIG. 3 is a schematic diagram illustrating a display device in an enlarged manner.

Given below is the explanation of the display device 30. FIG. 3 is a schematic diagram illustrating the relationship between the display device 30 and the user P after the couch top 14 has entered the tubular member 12. As illustrated in FIG. 3, the display device 30 includes a reflecting member 32, a display 34, a controller 36, and a holder 38. In the first embodiment, the display 34 further includes a projector 34A and a projection target member 34B having a display surface 34C.

The holder 38 fixes the projection target member 34B and the reflecting member 32 to the couch top 14. The projector 34A and the controller 36 are connected in either a wired manner or a wireless manner enabling them to send and receive information. The controller 36 sends the target image data for displaying to the projector 34A. Then, the projector 34A projects a light, which includes image information based on the received image data, toward the projection target member 34B. Herein, the projector 34A represents a projector, for example. Meanwhile, the projector 34A and the controller 36 can be configured in an integrated manner.

As long as the projection target member 34B represents a member capable of displaying (projecting) the light, which is projected from the projector 34A, on the display surface 34C; it serves the purpose. In the first embodiment, the explanation is given for an example in which the projection target member 34B represents a rear-projection screen that displays the images projected from the backside thereof on the display surface on the front side (i.e., the face opposite to the reflecting member 32). However, the projection target member 34B is not limited to be a rear-projection screen. The display surface 34C is positioned in between a focal point R (not illustrated in FIG. 3) of the reflecting member 32 and a reflecting surface T, and is positioned to face the reflecting surface T. Herein, the positioning of the display surface 34C to face the reflecting surface T implies the state in which the images displayed on the display surface 34C can be reflected from the reflecting surface T. Hence, the reflecting surface T and the display surface 34C are not limited to be positioned parallel to each other and facing each other, and can alternatively be positioned not to be parallel to each other.

The display surface 34C of the projection target member 34B either can be a flat surface or can be a curved surface. If the display surface 34C is a curved surface, it is desirable that the curved display surface 34C protrudes in the direction away from the reflecting member 32. More particularly, the display surface 34C can have a dome-like shape. Moreover, when the display surface 34C is a curved surface, the configuration can further include a correction lens as part of the projection lenses (not illustrated) disposed in the projector 34A. It is desirable that the correction lens is capable of performing correction in such a way that the light projected from the projector 34A is focused according to the shape of the display surface 34C. As a result of using such a correction lens, an in-focus image can be presented on the entire display surface 34C.

Although there is no restriction on the outer shape of the display surface 34C of the projection target member 34B, it is desirable that the outer shape is in line with the shape of the inner wall of the tubular member 12 and does not obstruct the positioning of the user P on the couch top 14 and the movement of the couch top 14 in the X-axis direction. Moreover, it is desirable that the size of the projection target member 34B in the Z-axis direction is such that a gap is maintained between the end of the projection target member 34B in the Z-axis direction and the inner wall of the tubular member 12.

Meanwhile, regarding a projection area A over which the projector 34A projects images, as long as the area A enables projection of images on the projection target member 34B at least on the side of a non-vertical direction than the central part of the couch top 14 in the Z-axis direction, it serves the purpose.

Meanwhile, the projector 34A can project, on the display surface 34C of the projection target member 34B, images having a greater projection size than the size of the display surface 34C. If an image having a greater projection size than the size of the display surface 34C is displayed on the display surface 34C, some portion of the image gets displayed also on the inner wall of the tubular member 12. That enables achieving more effective reduction in the cooped-up feeling of the user P.

The reflecting member 32 is fixed to the couch top 14 by the holder 38, and gets positioned inside the tubular member 12 accompanying the movement of the couch top 14. In the first embodiment, the explanation is given for a configuration in which the tubular member 12, which is cylindrical in shape, represents the member covering the couch top 14. However, that is not the only possible case. That is, the member covering the couch top 14 need not be circular, and can alternatively be rectangular, for example. Moreover, the member covering the couch top 14 need not cover the outer periphery of the reflecting member 32 over 360° in the Y-Z plane, and can be made of two flat surfaces, for example. Alternatively, the member covering the couch top 14 can be configured to cover the reflecting member 32 for at least some period of time while the couch top 14 enters the member.

The reflecting member 32 reflects the light that is displayed on the display surface 34C. If parallel light falls on the reflecting member 32, the light reflected from the reflecting member 32 converges at the focal point P. However, the light coming from the display surface 34C need not be parallel light.

Figure 4A:
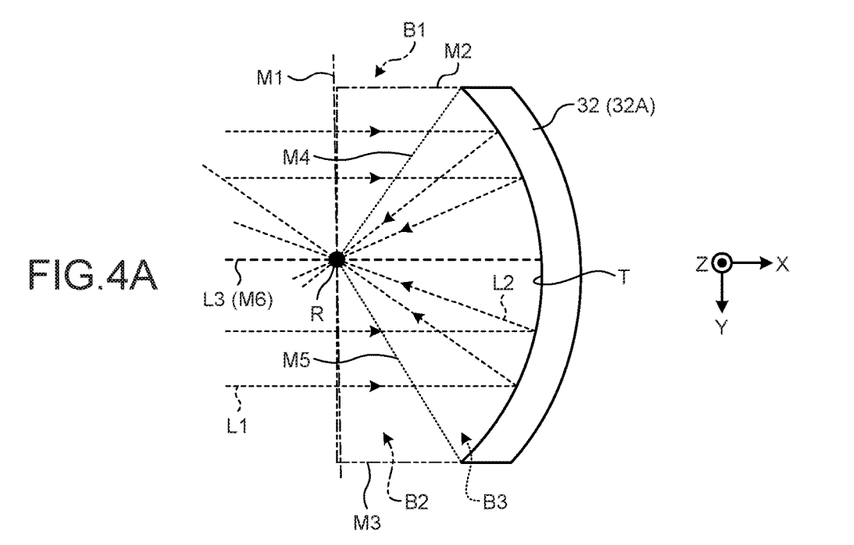
FIG. 4A is a schematic diagram illustrating an example of a reflecting member.

FIG. 4 is a schematic diagram illustrating the reflecting member 32. As illustrated in FIG. 4A, assume that parallel light L1 falls on the reflecting surface T of reflecting member 32. In that case, the parallel light L1 reflects from the reflecting surface T, and reflected light L2 converges at the focal point R. The reflecting surface T has such an optical property. Moreover, in the reflecting member 32, of the two surfaces that intersect with the incident parallel light L1 and that face each other, either the face on the side of the incidence of the parallel light L1 (i.e., the front face) can serve as the reflecting surface T or the other face (i.e., the reverse face) can serve as the reflecting surface T.

With respect to two virtual positions corresponding to the eyes of the user P who is lying down on the couch top 14, the reflecting member 32 and the display 34 are fixed by the holder 38 in such a way that the positional relationship explained below is satisfied. Thus, the holder 38 holds the reflecting member 32 and the display 34 (in the first embodiment, the projection target member 34B) in such a way that the positional relationship explained below is satisfied.

The two virtual viewpoint positions represent the supposed positions of the eyes of the user P who is lying down on the couch top 14. As far as the two viewpoint positions are concerned, the supposed positions of the eyes (the right eye and the left eye) of the user P in the three dimensional space above the couch top 14 are estimated in advance. Meanwhile, regarding the supposed positions of the eyes of the user P in the three-dimensional space, the two viewpoint positions corresponding to the eyes can be treated as a pair and a single position can be estimated in advance. Alternatively, a plurality of mutually different positions (that is, an area made of a plurality of position coordinates) can be estimated in advance.

The reflecting member 32 and the display 34 are disposed in such a way that both virtual viewpoint positions are present within a first area B1, which is the area formed between the focal point R and the reflecting surface T. More specifically, the first area B1 represents a three-dimensional space formed between a virtual two-dimensional plane M1 and the reflecting surface T. The virtual two-dimensional plane M1 represents a virtual two-dimensional plane passing through the focal point R and orthogonal to the X-axis direction of the couch top 14. In the following explanation, the two virtual viewpoint positions of the user P are simply referred to as the two viewpoint positions.

Meanwhile, in the first embodiment, the explanation is given on the premise that the X-axis direction of the couch top 14 is coincident with the light axis direction of a light axis L3.

Meanwhile, it is desirable that the reflecting member 32 and the display 34 are disposed in such a way that the two viewpoint positions are present within a second area B2 that lies inside the first area B1. Herein, the second area B2 lies inside the first area B1 and extends from one end to the other end of the reflecting surface T in the Y-axis direction of the couch top 14. In other words, the second area B2 represents a three-dimensional space formed on the inside of the virtual two-dimensional plane M1, a virtual two-dimensional plane M2, a virtual two-dimensional plane M3, and the reflecting surface T.

Herein, the virtual two-dimensional plane M2 represents a virtual two-dimensional plane passing through one end in the Y-axis direction of the reflecting surface T in the X-axis direction. The virtual two-dimensional plane M3 represents a virtual two-dimensional plane passing through the other end in the Y-axis direction of the reflecting surface T in the X-axis direction.

Hence, in this case, within the area formed by projecting the reflecting surface T onto the ZY plane (the plane formed along the Z-axis direction and the Y-axis direction), the points at which the two viewpoint positions are projected onto the ZY plane are positioned.

Moreover, it is desirable that the reflecting member 32 and the display 34 are disposed in such a way that the two viewpoint positions are positioned in two different areas formed by dividing the first area B1 with a virtual two-dimensional plane M6. Herein, the virtual two-dimensional plane M6 represents a virtual two-dimensional plane orthogonal to the Y-axis direction of the couch top 14 and running along the light axis L3 of the reflecting surface T. In other words, it is desirable to dispose the reflecting member 32 in such a way that the viewpoint positions of the right eye and the left eye of the user P are present in two different areas formed by division across the virtual two-dimensional plane M6.

Furthermore, it is desirable to dispose the reflecting member 32 and the display 34 in such a way that the two viewpoint positions are present within a third area B3, which lies inside the first area B1. The third area B3 is formed by a virtual two-dimensional plane M4, a virtual two-dimensional plane M5, and the reflecting surface T. The virtual two-dimensional planes M4 and M5 represent virtual two-dimensional planes that join both ends of the reflecting surface T in the Y-axis direction of the couch top 14 with the focal point R. That is, it is desirable to dispose the reflecting member 32 in such a way that the two viewpoint positions are present within the third area B3, which is a three-dimensional space on the inside of these virtual two-dimensional planes (the virtual two-dimensional planes M4 and M5) and the reflecting surface T.

Moreover, it is desirable to dispose the reflecting member 32 and the display 34 in such a way that the median plane of the user P, who is lying down on the couch top 14, is coincident with the light axis L3 of the reflecting surface T. More particularly, the median plane of the user P represents the XZ plane that passes through the middle of the two virtual viewpoint positions and that is formed by the X-axis direction and the Z-axis direction of the couch top 14.

In this way, it is desirable that the reflecting member 32 and the display 34 are disposed to exhibit the abovementioned positional relationship with respect to the two virtual viewpoint positions corresponding to the eyes of the user P who is lying on the couch top 14, and are fixed to the couch top 14. That is, the holder 38 desirably holds the reflecting member 32 and the display 34 in such a way that the positional relationship described above is satisfied.

Figure 4B:
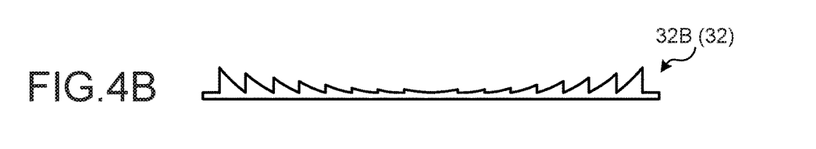
FIG. 4B is a schematic diagram illustrating another example of the reflecting member.
Figure 4C:
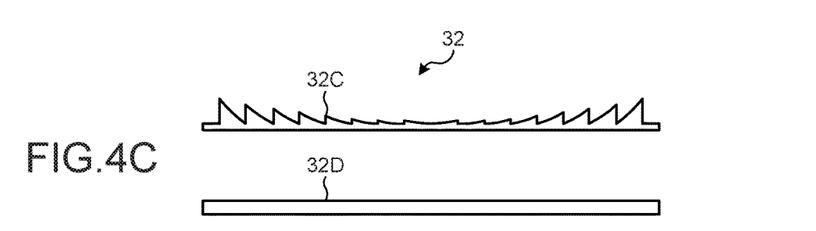
FIG. 4C is a schematic diagram illustrating still another example of the reflecting member.

As long as the reflecting member 32 has the optical property mentioned above, it serves the purpose. That is, the specific configuration of the reflecting member 32 is no object. For example, as illustrated in FIG. 4A, the reflecting member 32 represents a concave mirror 32A that has the reflecting surface T as an incident-direction concave surface for the light coming from the display surface 34C. Alternatively, as illustrated in FIG. 4B, the reflecting member 32 can represent a Fresnel mirror 32B. Still alternatively, the reflecting member 32 can be configured with a Fresnel lens 32C and a reflecting mirror 32D. As long as the positional relationship between the Fresnel lens 32C and the reflecting mirror 32D enables expression of the optical functions described above, it serves the purpose and is not limited to the positional relationship illustrated in FIG. 4C.

Meanwhile, from the perspective of configuring the reflecting member 32 to be thin and lightweight in nature, it is desirable to use the Fresnel mirror 32B as the reflecting member 32.

Herein, a Fresnel mirror implies a reflecting mirror in which a reflecting film is formed on a Fresnel lens, and has identical optical functions to a concave mirror.

The Fresnel mirror 32B is manufactured by forming a metallic film or a dielectric multi-layer film on the side of the concave-convex surface of a Fresnel lens. For example, weight saving can be achieved by using an optically-transparent resinous material such as acryl or polycarbonate as the Fresnel lens. However, the material used in the Fresnel lens is not limited to be transparent. When the Fresnel mirror 32B is transparent in nature, the Fresnel surface can be oriented to the opposite side of the projector 34C. In that case, the Fresnel lens serving as the base member of the Fresnel mirror 32B can be manufactured as a convex lens.

From the perspective of reducing the weight while holding down the flexure, it is desirable that the Fresnel mirror 32B has the thickness in the range of 2 mm to 5 mm. Moreover, it is desirable that the Fresnel mirror 32B has the reflectance of 70% or more, for example.

Meanwhile, the Fresnel mirror 32B can be manufactured by directly processing the Fresnel shape on the surface of a metallic material.

There is no restriction on the material used in forming the reflecting film on the surface of the Fresnel lens in the Fresnel mirror 32B. However, in the case in which the display device 30 including the Fresnel mirror 32B is to be installed in the medical diagnostic imaging unit 11; from the perspective of holding down the magnetic field effect, it is desirable that the reflecting film is made of a vapor deposited film of aluminum having the thickness equal to or smaller than 100 nm. Alternatively, it is desirable that a dielectric multi-layer film ($SiO_2$, $TiO_2$, or a laminated film of some other oxide) is used as the reflecting film.

Although there is no restriction on the shape of the reflecting member 32, it is desirable that the shape is in line with the shape of the inner wall of the tubular member 12 and does not obstruct the positioning of the user P on the couch top 14 and the movement of the couch top 14 in the X-axis direction.

Meanwhile, it is desirable that the size of the reflecting member 32 in the Z-axis direction is such a gap is maintained between the reflecting member 32 and the inner wall of the tubular member 12.

Regarding the size of the reflecting member 32 in the Y-axis direction, when the tubular member 12 has the internal diameter of, for example, 60 cm to 70 cm, it is desirable that the size of the reflecting member 32 in the Y-axis direction is equivalent to the viewing angle equal to or greater than 60° of the user P who is lying down facing upwards on the couch top 14. If the size of the reflecting member 32 in the Y-axis direction is set to be equivalent to the viewing angle equal to or greater than 60°, it becomes possible to reduce the cooped-up feeling of the user P inside the tubular member 12. Regarding the reflecting surface T, the size in the X-axis direction can be set to cover at least the portion from the top of the head to the position between the eyes and the nose of the user P who is lying on the couch top 14. With that size, the inner wall of the tubular member 12 can be prevented from entering the downward field of view of the user P.

The holder 38 fixedly holds the projection target member 34B and the reflecting member 32 in such a way that the display surface 34C faces the reflecting surface T in between the focal point R and the reflecting surface T. Moreover, the holder 38 holds the reflecting member 32 and the display surface 34C at such positions and angles that the reflecting surface T is visible to the user P who is lying down facing upwards on the couch top 14. Furthermore, the holder 38 holds the reflecting member 32 and the display 34 in such a way that the positional relationship described above is exhibited with respect to the two virtual viewpoint positions corresponding to the eyes of the user P who is lying on the couch top 14.

In the first embodiment, of the two ends of the couch top 14 in the X-axis direction, the holder 38 is disposed at the end that is inserted first in the tubular member 12 (hereinafter, called the end on the side of head of the user P). That is, the holder 38 holds the reflecting member 32 and the display surface 34C at the end on the side of the head of the user P who is lying on the couch top 14. Meanwhile, the holder 38 can further include an adjustment mechanism for adjusting the angle (the inclination with respect to the Z-axis direction) of the reflecting member 32. In that case, the angle of the reflecting member 32 can be adjusted in tune with the positions of the eyes of the user P who is lying down on the couch top 14.

In the case of a configuration in which the medical diagnostic imaging unit 11 includes a head coil that is put on the head of the user P during the diagnosis of the head, the reflecting member 32 and the display surface 34C can be held in such a way that the head coil satisfies the positional relationship described below. Alternatively, in order to ensure that the positional relationship described below is satisfied, the holder 38 can fix the head coil and the reflecting member 32, while the couch top 14 can hold the display surface 34C.

For that reason, the reflecting member 32 and the projection target member 34B move accompanying the movement of the couch top 14 in the X-axis direction, and are either inserted to the inside of the tubular member 12 or carried to the outside of the tubular member 12. Thus, the driver 16 moves the couch top 14, and changes the distance from the projector 34A to the projection target member 34B, and the reflecting member 32.

Meanwhile, when the display 34 is disposed inside a magnetic-field space such as the tubular member 12, there are times when the images displayed on the display surface 34C get distorted due to the magnetic field effect. Hence, from the perspective of holding down the magnetic field effect on the displayed images, it is desirable that the display 34 is configured with the projector 34A and the projection target member 34B, and that the projector 34A is disposed on the outside of the tubular member 12.

Meanwhile, as long as the display 34 is capable of displaying images on the display surface 34C, it serves the purpose and the configuration thereof is not limited to include the projector 34A. Examples of the display 34 include a liquid crystal display (LCD) or an organic electroluminescence (EL).

Figure 5:
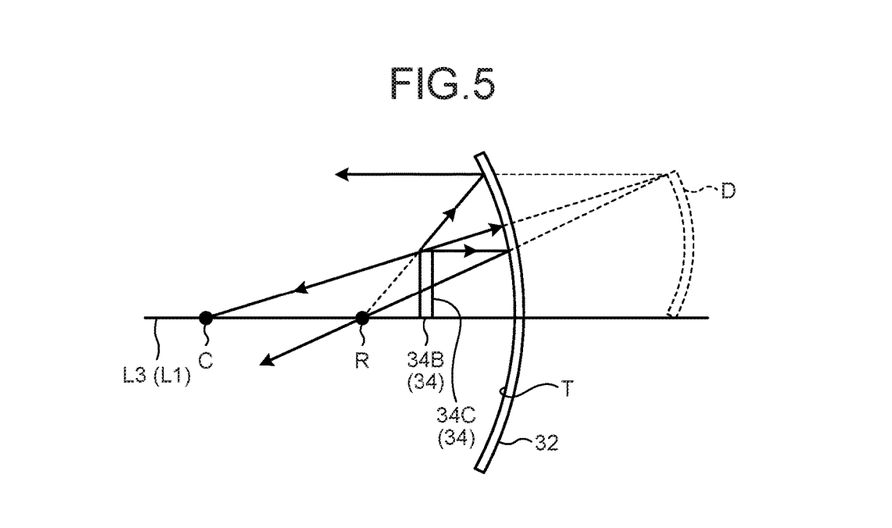
FIG. 5 is a schematic diagram illustrating the positional relationship between a display surface and a reflecting surface.

FIG. 5 is a schematic diagram illustrating the positional relationship between the display surface 34C of the display 34 and the reflecting surface T according to the first embodiment. As illustrated in FIG. 5, the display surface 34C is disposed in between the focal point R of the reflecting member 32 and the reflecting surface T of the reflecting member 32. When the reflecting surface T of the reflecting member 32 is a concave surface, the display surface 34C is disposed closer to the reflecting surface T than to the focal point R.

For that reason, when the user P views the reflecting surface T, he or she happens to view an erected virtual image D of the image displayed on the display surface 34C. Herein, it is desirable that the erected virtual image D is formed by enlarging the image displayed on the display surface 34C.

Figure 6:
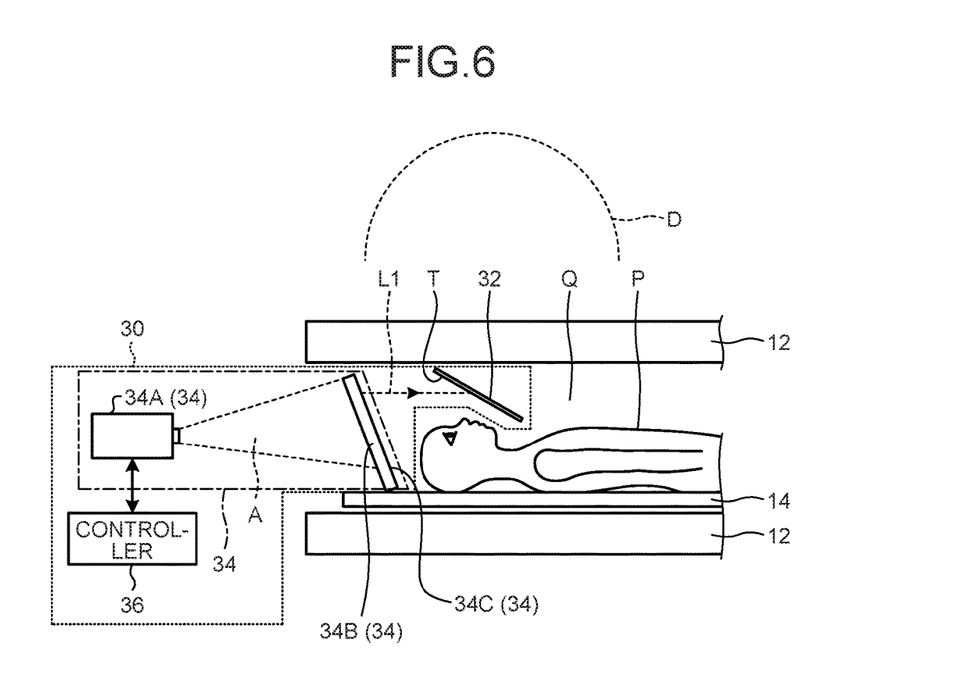
FIG. 6 is a schematic diagram illustrating a state in which the couch top is inserted deep inside the tubular member.

FIG. 6 is a schematic diagram illustrating a state in which the couch top 14, on which the user P is lying down, is inserted deep inside the tubular member 12.

As illustrated in FIG. 6, at the end on the side of the head of the user P in the X-axis direction of the couch top 14, the reflecting member 32 and the projection target member 34B are held by the holder 38 (not illustrated in FIG. 6) in such a way that the positional relationship described above is satisfied. The position of the head of the user P, who is lying on the couch top 14, is adjusted in such a way that the reflecting member 32 becomes viewable.

The projector 34A projects images on the display surface 34C of the projection target member 34B under the control of the controller 36. In the first embodiment, the explanation is given for an example in which the projector 34A projects images on the display surface 34C, which represents the surface of the projection target member 34B which is on the opposite side of the reflecting member 32 (i.e., on the side of the projector 34A). Meanwhile, as described earlier, the surface on the side of the reflecting member 32 can also be treated as the display surface 34C.

Hence, when the user P, who is lying on the couch top 14, views the reflecting surface T of the reflecting member 32, he or she happens to view the erected virtual image D of the image that is projected on the display surface 34C of the projection target member 34B.

Then, once the couch top 14 is inserted inside the tubular member 12, the reflecting member 32 and the projection target member 34B also get inserted inside accompanying the movement of the couch top 14. Under the control of the controller 36, the projector 34A projects images on the display surface 34C of the projection target member 34B on a continuing basis.

For that reason, in the state in which the couch top 14 is on the outside of the tubular member 12, in the state in which the couch top 14 is moving, and in the state in which the couch top 14 has been inserted inside the tubular member 12 from the outside; the user P can view the reflecting surface T of the reflecting member 32 and view the erected virtual image D of the image projected on the display surface 34C of the projection target member 34B. That is, also inside the tubular member 12, the user can view the erected virtual image D. Moreover, since the erected virtual image D is formed in the distance from the inner wall of the tubular member 12, there is a decrease in the oppressive feeling brought to the user P.

Hence, inside the tubular member 12 too, the display device 30 can be used in reducing the burden on the user.

Meanwhile, if the erected virtual image D is a convex image protruding toward the side of the user P, then there are times when the user P has an oppressive feeling. The reason for the fact that the erected virtual image D is viewed as a convex image is the occurrence of binocular parallax.

For that reason, it is desirable that the angle of convergence of the erected virtual image D, which is viewed via the reflecting surface T from the two virtual viewpoint positions corresponding to the eyes of the user P, at the central part of the reflecting surface T of the reflecting member 32 is smaller than the angles of convergence at the ends of the reflecting surface T. When the angle of convergence at the central part of the reflecting surface T is smaller than the angles of convergence at the ends, the erected virtual image D is viewed as a concave image protruding in the direction away from the user P.

In order to reduce the angle of convergence at the central part of the reflecting surface T of the reflecting member 32 as compared to the angles of convergence at the ends, the reflecting surface T can be set as an aspheric surface approximated by a quadratic expression.

Figure 7:
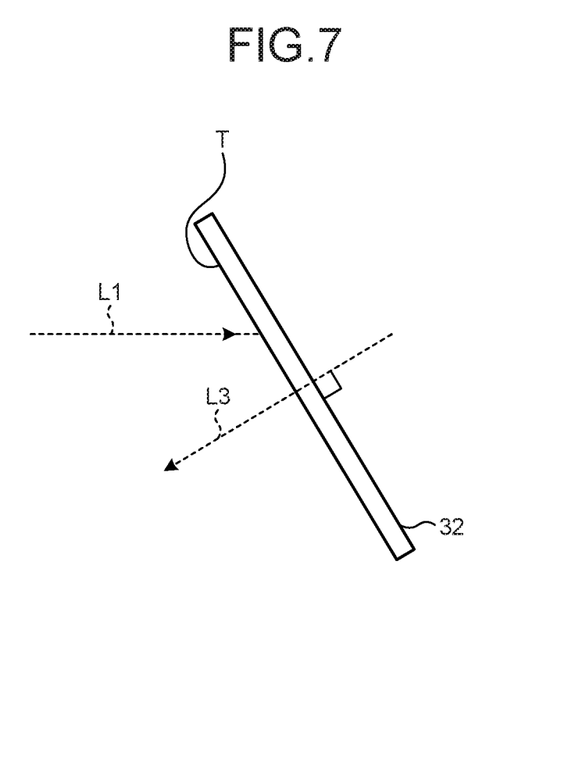
FIG. 7 is a schematic diagram illustrating the relationship between the reflecting member and incident light.

Meanwhile, it is desirable that the light axis direction L3 of the reflecting surface T of the reflecting member 32 is not coincident with the incident direction of the light falling on the reflecting surface T. FIG. 7 is a schematic diagram illustrating the relationship between the light axis direction L3 of the reflecting member 32 and the incident light L1.

As illustrated in FIG. 7, it is desirable that the light axis direction L3 of the reflecting surface T of the reflecting member 32 is not coincident with the incident direction of the incident light L1 falling in the reflecting surface T.

In order to ensure that the light axis direction L3 of the reflecting surface T is not coincident with the incident light L1, the holder 38 can hold the projection target member 34B and the reflecting member 32 in such a manner that the relationship is satisfied. Meanwhile, when the reflecting member 32 includes the Fresnel mirror 32B or the Fresnel lens 32C, the optical center of the Fresnel mirror 32B or the Fresnel lens 32C can be shifted (decentered) with respect to the viewpoint position in the reflecting member 32.

The viewpoint position in the reflecting member 32 represents the point of intersection between the vertical line passing through a recommended position on the couch top 14 and the reflecting member 32. Herein, the recommended position represents the position at which the eyes of the user P, who is lying facing upward on the couch top 14, are recommended to be positioned; and can be set in advance.

If the light axis direction L3 of the reflecting surface T is not coincident with the incident light L1, then it becomes possible to enhance the image quality of the erected virtual image D viewed by the user P.

Meanwhile, in order to reduce the cooped-up feeling of the user P in a more effective manner, it is desirable that the erected virtual image D is viewed at a position separated from the viewpoint of the user P by one meter or more. In order to make the erected virtual image D viewable at a position separated from the viewpoint of the user P by one meter or more, it is desirable that the angle of convergence for the user, who is looking at the reflecting surface T, is equal to or smaller than 4°.

In order to set the angle of conversion to be equal to or smaller than 4°, it is desirable that the focal length of the reflecting member 32 is set to be equal to or greater than 300 mm.

When the reflecting member 32 is configured with the concave mirror 32A (see FIG. 4A), the focal length of the reflecting member 32 represents the focal length of the concave mirror 32A. When the reflecting member 32 is configured with the Fresnel mirror 32B (see FIG. 4B), the focal length of the reflecting member 32 represents the focal length of the Fresnel mirror 32B. When the reflecting member 32 is configured with the Fresnel lens 32C and the reflecting mirror 32D (see FIG. 4C), the focal length of the reflecting member 32 represents the focal length of the Fresnel lens 32C.

Meanwhile, the reflecting surface T of the reflecting member 32 is, for example, a paraboloid approximated by a quadratic expression.

More particularly, the reflecting surface T of the reflecting member 32 is a paraboloid approximated by Equation (1).

$$\frac{x^2}{2R} + a_1 x^4 + a_2 x^6 \tag{1}$$

In Equation (1), R represents a quadratic coefficient for deciding the predominant concave shape of the reflecting member 32; α1 represents a fourth-order coefficient for correcting the shape of the reflecting member 32; and α2 represents a sixth-order coefficient for further correcting the shape of the reflecting member 32.

Meanwhile, in the case of using the Fresnel mirror 32B as the reflecting member 32, in order to ensure the necessary capability, it is desirable to perform approximation up to the sixth-order equation. Moreover, in order to enhance the image formation capability of the reflecting member 32, it is also possible to perform approximation up to the equation of a higher order.

In the display device 30 according to the first embodiment, in the case of setting the angle of convergence to be equal to or smaller than 4° and adjusting the erected virtual image D to be viewable at a position separated from the viewpoint of the user P by one meter or more, for example, the curved surface of the erected virtual image D is set to have a curvature of 497.534 mm, the distance between the erected virtual image D and the viewpoint of the user P is set to 1169 mm, the angle between the reflecting surface T of the reflecting member 32 and the horizontal direction is set to 29.8°, and the eccentricity is set to 2.6 mm. With such a configuration, the angle of convergence for the user P can be set to 3.4°. At that time, in Equation (1), the value of R is 1268.487, the value of α1 is $1.3 \times 10^{-9}$, and the value of α2 is $-2.44 \times 10^{-15}$.

As described above, the display device 30 according to the first embodiment includes the reflecting member 32 and the display 34. The reflecting member 32 is fixed to the couch top 14 on which the user P is asked to lie down. Moreover, the reflecting member 32 has the reflecting surface T, which is reflective in nature and which has the optical property that the reflected light of incident parallel light is focused at the focal point R. The display 34 includes the display surface 34C on which images are displayed. The display surface 34C is fixed to the couch top 14 in between the focal point R and the reflecting surface T, and faces the reflecting surface T.

Hence, by viewing the reflecting surface T, the user P can view the erected virtual image D of the image displayed on the display surface 34C.

Thus, the display device 30 according to the first embodiment enables achieving reduction in the cooped-up feeling of the user P.

The reflecting member 32 has the optical property that the reflected light of incident parallel light is focused at a focal point. Moreover, the display surface 34C of the display 34 is positioned in between the focal point R and the reflecting surface T, and is positioned to face the reflecting surface T. For that reason, by viewing the reflecting surface T, the user P can sometimes view the erected virtual image D that is formed by enlarging the image displayed on the display surface 34C.

In that case, the display device 30 according to the first embodiment can present the user P with the erected virtual image D, which has a larger field of view than the image displayed on the display 34.

As a method for displaying images without making the user P conscious about the inner wall of the tubular member 12, in order to ensure that the inner wall of the tubular member 12 is not viewed by the user P, it is possible to think of further shortening the distance between the projection target member 34B and the reflecting member 32. However, as the distance between the projection target member 34B and the reflecting member 32 is shortened, the distance between the head of the user P and the projection target member 34B also gets shortened, and the projection target member 34B may bring an oppressive feeling to the user P.

On the other hand, the display device 30 according to the first embodiment can present the erected virtual image D to the user P. For that reason, the display device 30 can reduce the cooped-up feeling of the user P without causing an oppressive feeling attributed to the projection target member 34B.

Meanwhile, in the first embodiment, the explanation is given for an example in which the display device 30 is installed in the medical diagnostic imaging device 10. However, the display device 30 is not limited to be installed in the medical diagnostic imaging unit 11. For example, the display device 30 can be disposed in various types of spaces. In that case, the reflecting member 32 of the display device 30 can be disposed at a position at which the reflecting member 32 satisfies the abovementioned conditions and is viewable to the user P present inside the concerned space.

Second Embodiment

Figure 8:
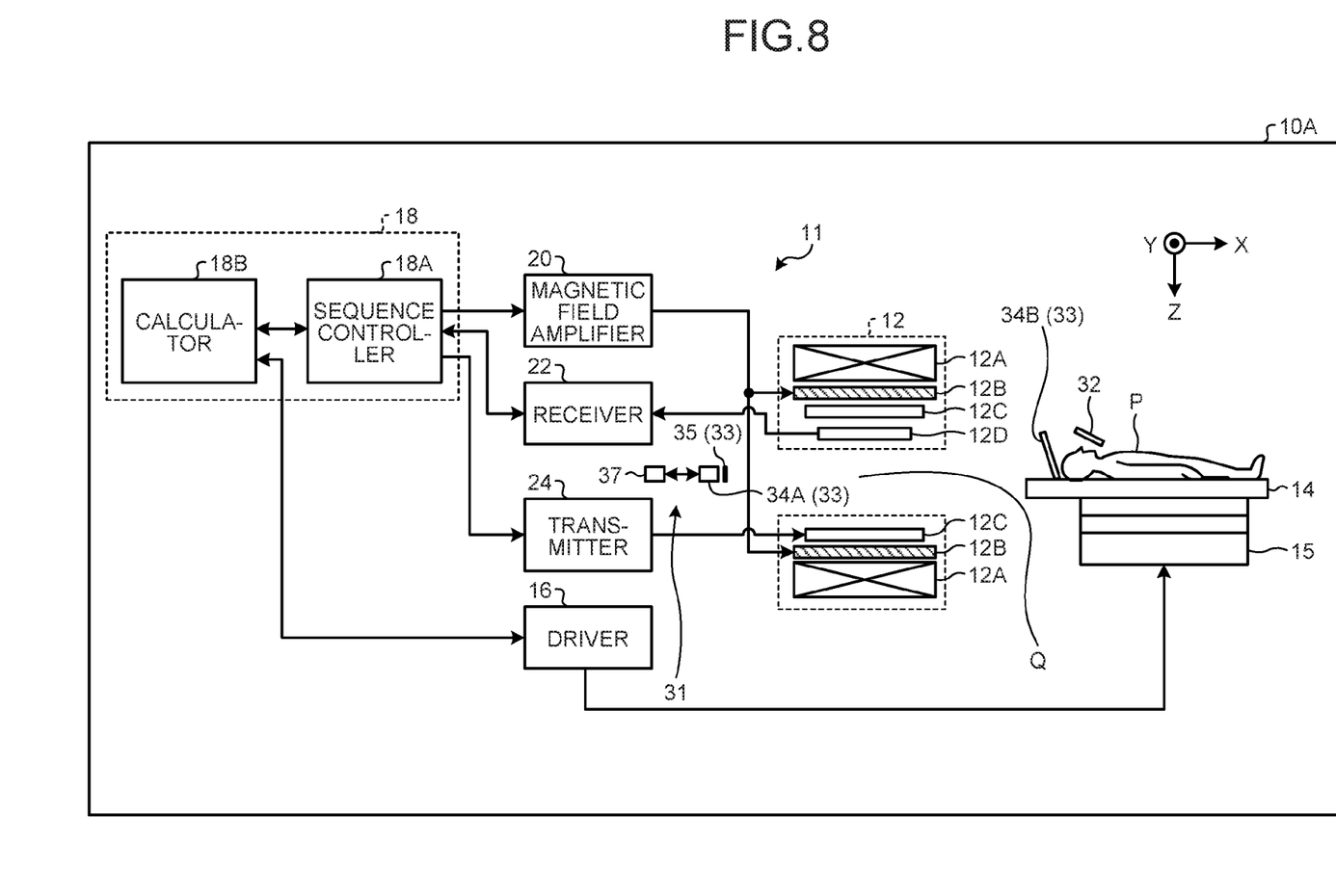
FIG. 8 is a schematic diagram illustrating an example of a medical diagnostic imaging device.

FIG. 8 is a schematic diagram illustrating an example of a medical diagnostic imaging device 10A according to a second embodiment. The medical diagnostic imaging device 10A includes the medical diagnostic imaging unit 11 and a display device 31. Herein, the medical diagnostic imaging unit 11 is identical to the first embodiment.

Figure 9:
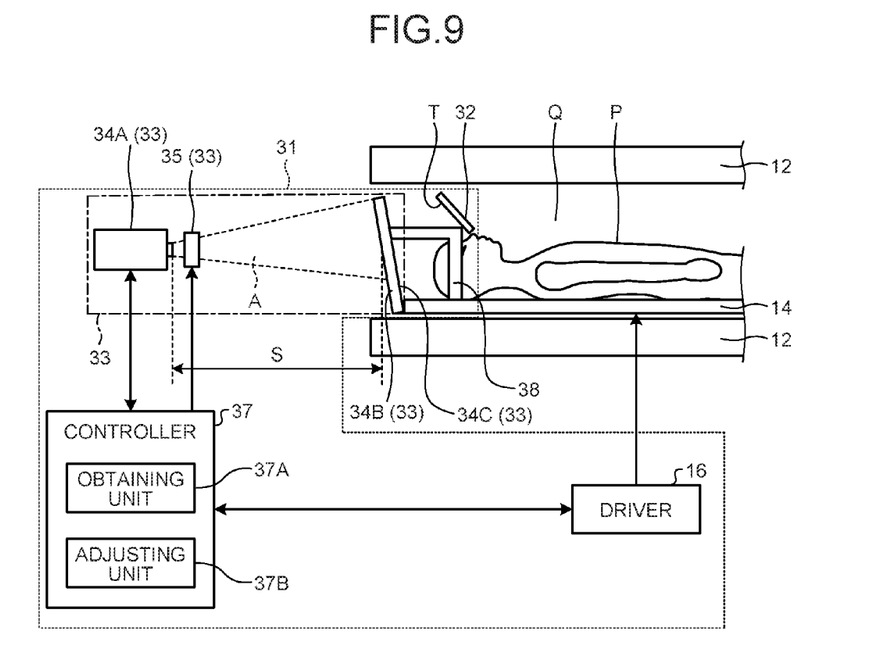
FIG. 9 is a schematic diagram illustrating the display device.

FIG. 9 is a schematic diagram illustrating the relationship between the display device 31 and the user P when the couch top 14 has entered the tubular member 12. The display device 31 includes the reflecting member 32 and a display 33. Moreover, the display 33 includes the projector 34A, the projection target member 34B, an adjusting unit 35, and a controller 37.

The projector 34A and the projection target member 34B are identical to the first embodiment. Moreover, in an identical manner to the first embodiment, the projector 34A and the projection target member 34B are held by the holder 38 at the end on the side of head of the user P who is lying on the couch top P. Furthermore, the positional relationship between the projector 34A and the projection target member 34B is identical to the first embodiment.

The adjusting unit 35 is a mechanism for varying the focal point and the projection size of the images projected from the projector 34A onto the projection target member 34B. The adjusting unit 35 is a zoom lens, for example.

The controller 37 is connected to the projector 34A, the adjusting unit 35, and the driver 16. The controller 37 sends image data of the target image for displaying to the projector 34A. Moreover, the controller 37 sends adjustment information to the adjusting unit 35. The projector 34A projects the image corresponding to the received image data on the display surface 34C. The adjusting unit 35 adjusts the focal point and the projection size of the image according to the adjustment information received from the controller 37.

The controller 37 includes an obtaining unit 37A and an adjusting unit 37B. One or both of the obtaining unit 37A and the adjusting unit 37B can be, for example, implemented by making a processor such as a central processing unit (CPU) to execute computer programs, that is, implemented using software; or implemented using hardware such as an integrated circuit (IC); or implemented using a combination of software and hardware.

The obtaining unit 37A obtains a distance S from the projector 34A to the projection target member 34B and the reflecting member 32. The distance S represents the shortest distance along the X-axis direction between the light outgoing surface for images on the projector 34A and the display surface 34C of the projection target member 34B. Herein, the X-axis direction represents the X-axis of the light that reaches the display surface 34C from the projector 34A.

As explained in the first embodiment, the driver 16 moves the couch top 14, and changes the distance S from the projector 34A to the projection target member 34B and the reflecting member 32. The obtaining unit 37A obtains the distance S from the driver 16, for example.

Alternatively, the obtaining unit 37A can obtain the distance S from an operating unit (not illustrated). In that case, upon receiving input of the distance S via an operation instruction from the user, the operating unit can output the distance S to the obtaining unit 37A.

Still alternatively, the display device 30 can be configured to include a separate sensor for measuring the distance S. In that case, the obtaining unit 37A can obtain the distance S from that sensor.

According to the distance S obtained by the obtaining unit 37A, the adjusting unit 37B adjusts at least either the projection size, or the luminance, or the focal point of the image, which is projected on the display surface 34C of the projection target member 34B, in such a way that predetermined projection conditions are satisfied. The projection conditions include, for example, at least either a standard projection size, or a standard luminance, or a standard image focus.

For example, the adjusting unit 37B adjusts the luminance of each pixel in the image data, which is sent to the projector 34A, in such a way that an image having the standard luminance is projected onto the display surface 34C. Then, the controller 37 sends the post-correction image data to the projector 34A.

More particularly, in order to ensure that an image having the standard luminance is projected onto the display surface 34C, the adjusting unit 37B corrects the luminance of each pixel in the image data in such a way that, for example, longer the distance S, higher is the luminance; and shorter the distance S, lower is the luminance. Then, the controller 37 sends the post-correction image data to the projector 34A.

Hence, regardless of the distance S, images having a certain luminance (the standard luminance) are projected onto the display surface 34C.

Moreover, for example, according to the distance S, the adjusting unit 37B adjusts the adjusting unit 35 in such a way that the image having the standard projection size and the standard image focus is projected onto the display surface 34C. For that reason, regardless of the distance S, images having a certain projection size (the standard projection size) and being in focus are projected onto the display surface 34C.

Figure 10:
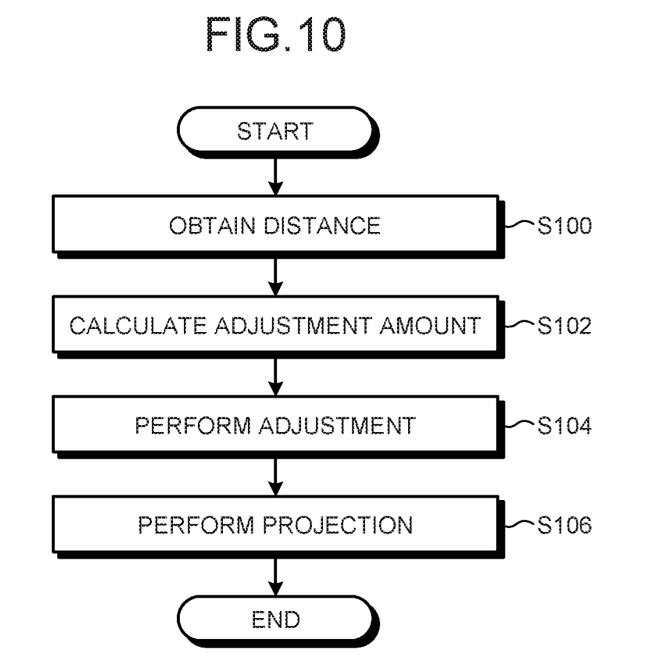
FIG. 10 is a flowchart for explaining an exemplary sequence of operations performed in a controller.

FIG. 10 is a flowchart for explaining an exemplary sequence of operations performed in the controller 37 according to the second embodiment.

Firstly, the obtaining unit 37A obtains the distance S (Step S100). Then, according to the distance S obtained at Step S100, the adjusting unit 37B calculates the adjustment amount for performing adjustment to satisfy predetermined projection conditions (Step S102). For example, the adjusting unit 37B calculates the correction value regarding the luminance of each pixel and the adjustment amount for the adjusting unit 35.

Subsequently, according to the distance S obtained by the obtaining unit 37A at Step S100, the adjusting unit 37B adjusts at least either the projection size, or the luminance, or the focal point of the image, which is projected on the display surface 34C of the projection target member 34B, in such a way that predetermined projection conditions are satisfied (Step S104). For example, according to the adjustment amount calculated at Step S102, the adjusting unit 37B corrects the luminance of each pixel in the image data and adjusts the adjustment amount to be sent to the adjusting unit 35.

Then, the controller 37 outputs the post-correction image data to the display 33 and instructs the display 33 to project the image (Step S106). As a result of performing the operation at Step S106, the image satisfying the predetermined projection conditions is projected onto the display surface 34C. That marks the end of the present routine.

As described above, the display device 31 according to the second embodiment includes the obtaining unit 37A and the adjusting unit 37B. The obtaining unit 37A obtains the distance S from the projector 34A to the projection target member 34B and the reflecting member 32. Then, according to the distance S, the adjusting unit 37B adjusts at least either the projection size, or the luminance, or the focal point of the image, which is projected on the display surface 34C of the projection target member 34B, in such a way that predetermined projection conditions are satisfied.

Thus, in the display device 31 according to the second embodiment, in addition to achieving the effect that is achieved in the first embodiment, also in the case in which the distance S changes, the erected virtual image D can be presented to the user P without causing a sense of discomfort.

Figure 11:
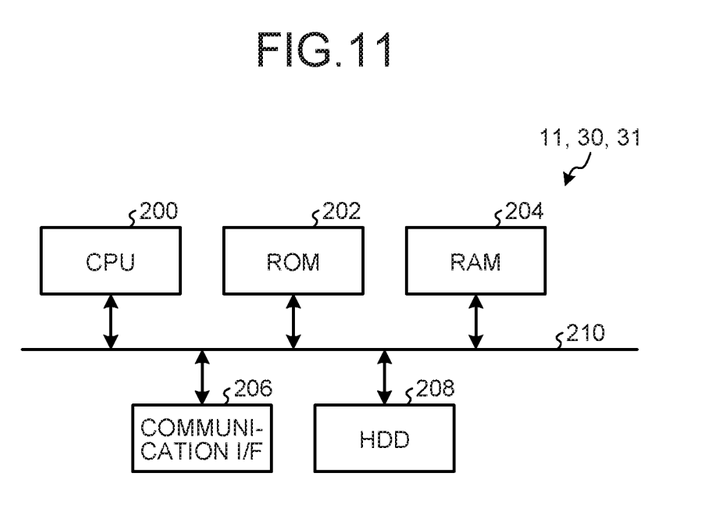
FIG. 11 is a block diagram illustrating an exemplary hardware configuration.

Given below is the explanation of a hardware configuration of the medical diagnostic imaging unit 11, the display device 30, and the display device 31 according to the embodiments described above. FIG. 11 is a block diagram illustrating an exemplary hardware configuration of the medical diagnostic imaging unit 11, the display device 30, and the display device 31 according to the embodiments described above.

The medical diagnostic imaging unit 11, the display device 30, and the display device 31 according to the embodiments described above have the hardware configuration of a general-purpose computer that includes a central processing unit (CPU) 200, a read only memory (ROM) 202, a random access memory (RAM) 204, a communication interface (I/F) 206, and a hard disk drive (HDD) 208. Herein, the CPU 200, the ROM 202, the RAM 204, the communication I/F 206, and the HDD 208 are connected to each other by a bus 210.

The computer programs executed for performing operations of the medical diagnostic imaging unit 11, the display device 30, and the display device 31 according to the embodiments described above are stored in advance in the ROM 202.

Alternatively, the computer programs executed for performing operations of the medical diagnostic imaging unit 11, the display device 30, and the display device 31 according to the embodiments described above can be recorded as installable or executable files in a computer-readable recording medium such as a compact disk read only memory (CD-ROM), a floppy (registered trademark) disk, a compact disk recordable (CD-R), or a digital versatile disk (DVD).

Still alternatively, the computer programs executed for performing operations of the medical diagnostic imaging unit 11, the display device 30, and the display device 31 according to the embodiments described above can be stored in a computer connected to a network such as the Internet and can be downloaded via the network. Still alternatively, the computer programs executed for performing operations of the medical diagnostic imaging unit 11, the display device 30, and the display device 31 according to the embodiments described above can be distributed via a network such as the Internet.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A display device comprising:
    a reflecting member having a reflecting surface that is an aspheric surface, and having an optical property that reflected light of parallel light incident on the reflecting surface is focused to a focal point, the reflecting member being fixed to a couch top configured for a user to lie down on; and
    a display having a display surface for displaying an image, the display being fixed to the couch top so that the display surface is positioned between the focal point and the reflecting surface to face the reflecting surface, wherein
    the reflecting member and the display are disposed so that two virtual viewpoint positions corresponding to eyes of the user are present within a first area formed in between the focal point and the reflecting surface.

2. The device according to claim 1, wherein the reflecting member and the display are disposed so that the two virtual viewpoint positions are present within a second area that is present inside the first area and which extends from one end to the other end of the reflecting surface in a Y-axis direction of the couch top.

3. The device according to claim 1, wherein the reflecting member and the display are disposed so that the two virtual viewpoint positions are present within two different areas into which the first area is divided with a virtual two-dimensional plane which is orthogonal to a Y-axis direction of the couch top and which runs along a light axis of the reflecting surface.

4. The device according to claim 1, wherein the reflecting member and the display are disposed so that the two virtual viewpoint positions are present within a second area that is formed by the reflecting surface and two virtual two-dimensional planes that join both ends of the reflecting surface in a Y-axis direction of the couch top with the focal point.

5. The device according to claim 1, wherein the reflecting member and the display are disposed so that a median plane of the user is coincident with a light axis of the reflecting surface.

6. The device according to claim 1, wherein the reflecting member is a concave mirror.

7. The device according to claim 1, wherein the reflecting member is a Fresnel mirror.

8. The device according to claim 1, wherein an angle of convergence of an erected virtual image that is viewable via the reflecting surface from the two virtual viewpoint positions for the user at a central part of the reflecting surface is smaller than angles of convergence at ends of the reflecting surface.

9. The device according to claim 1, wherein a light axis direction of the reflecting surface is not coincident with an incident direction of light falling on the reflecting surface.

10. The device according to claim 1, wherein the display includes
    a projection target member having the display surface, and
    a projector configured to project the image on the display surface.

11. The device according to claim 10, wherein the projector is configured to project, on the display surface, the image having a greater projection size than the display surface.

12. The device according to claim 10, further comprising a driver configured to vary distance from the projector to the projection target member and the reflecting member.

13. The device according to claim 12, wherein the display includes control circuitry configured to:
    obtain the distance, and
    adjust, according to the distance, at least one of projection size, luminance, and focal point of the image that is projected on the display surface of the projection target member, in such a way that a predetermined projection condition is satisfied.

14. A medical diagnostic imaging device comprising:
    a tubular member including a magnetic field generation source for forming a magnetic-field space;

a couch top configured for a user to lie down on;

a driver configured to move the couch top to inside or outside of the tubular member;

a reflecting member having a reflecting surface that is an aspheric surface, and having an optical property that reflected light of parallel light incident on the reflecting surface is focused to a focal point, the reflecting member being fixed to the couch top; and a display having a display surface for displaying an image, the display being fixed to the couch top so that the display surface is positioned between the focal point and the reflecting surface to face the reflecting surface, wherein the reflecting member and the display are disposed so that two virtual viewpoint positions corresponding to eyes of the user are present within a first area formed in between the focal point and the reflecting surface.

15. The device according to claim 8, wherein the angle of the convergence is equal to or smaller than 4 degrees.

* * * * *